(12) United States Patent
Schmalz

(10) Patent No.: US 9,001,318 B2
(45) Date of Patent: Apr. 7, 2015

(54) SOILING CHECK OF THE WINDOW OF A MEASURING APPARATUS FOR CHECKING SHEET MATERIAL

(75) Inventor: Steffen Schmalz, Munich (DE)

(73) Assignee: Giesecke & Devrient GmbH, Munich (DE)

( * ) Notice: Subject to any disclaimer, the term of this patent is extended or adjusted under 35 U.S.C. 154(b) by 27 days.

(21) Appl. No.: 13/996,207

(22) PCT Filed: Dec. 19, 2011

(86) PCT No.: PCT/EP2011/006415
§ 371 (c)(1),
(2), (4) Date: Jun. 20, 2013

(87) PCT Pub. No.: WO2012/084183
PCT Pub. Date: Jun. 28, 2012

(65) Prior Publication Data
US 2013/0271753 A1   Oct. 17, 2013

(30) Foreign Application Priority Data
Dec. 21, 2010   (DE) .................. 10 2010 055 428

(51) Int. Cl.
*G01N 21/00* (2006.01)
*G01N 21/15* (2006.01)
*G01N 21/88* (2006.01)
*G01N 21/86* (2006.01)
*G07D 7/18* (2006.01)

(52) U.S. Cl.
CPC ............ *G01N 21/8806* (2013.01); *G01N 21/86* (2013.01); *G01N 2021/157* (2013.01); *G07D 7/187* (2013.01)

(58) Field of Classification Search
USPC .......... 356/237.1–237.5, 238.1, 238.3, 239.1, 356/429–431, 71; 250/548, 556, 559.42, 250/559.44–559.46, 559.01, 559.16–559.18
See application file for complete search history.

(56) References Cited

U.S. PATENT DOCUMENTS

| | | | | |
|---|---|---|---|---|
| 4,352,988 A | * | 10/1982 | Ishida | 250/559.11 |
| 4,435,834 A | * | 3/1984 | Pauli et al. | 382/135 |
| 4,723,072 A | * | 2/1988 | Naruse | 235/454 |
| 5,164,601 A | * | 11/1992 | Nordstrom | 250/556 |

(Continued)

FOREIGN PATENT DOCUMENTS

| | | |
|---|---|---|
| DE | 3816943 A1 | 11/1989 |
| DE | 40 22 020 A1 | 1/1992 |

(Continued)

OTHER PUBLICATIONS

International Search Report in PCT/EP2011/006415, Apr. 2, 2012.
Search Report in German Patent Application 10 2010 055 428.6, Apr. 1, 2011.
International Preliminary Report on Patentability and Written Opinion in PCT/EP2011/006415, Jun. 25, 2013.

*Primary Examiner* — Hoa Pham
(74) *Attorney, Agent, or Firm* — Workman Nydegger

(57) ABSTRACT

A method carries out a soiling check of the measurement window of a measuring device for checking sheet material. A measuring device carries out the method. A device for processing a sheet material comprises the measuring device. The soiling check uses, only areas of the measurement window which correspond, in terms of width and position in the beam path of a light, to the areas of the checked sheet material which are checked during the checking of the sheet material. As a result, fewer cleaning steps are needed for the measurement window.

15 Claims, 2 Drawing Sheets

(56) References Cited

U.S. PATENT DOCUMENTS

| | | | |
|---|---|---|---|
| 5,280,333 A | 1/1994 | Wunderer | |
| 6,101,266 A * | 8/2000 | Laskowski et al. | 382/135 |
| 6,472,670 B1 | 10/2002 | Philipp et al. | |
| 7,414,710 B2 | 8/2008 | Wunderer et al. | |
| 8,107,712 B2 * | 1/2012 | Holl | 382/135 |
| 8,421,046 B2 * | 4/2013 | Leuthold | 250/556 |
| 8,649,069 B2 * | 2/2014 | Okawa et al. | 358/474 |
| 2002/0092800 A1 | 7/2002 | Philipp et al. | |
| 2010/0000312 A1 | 1/2010 | Nommer et al. | |
| 2011/0180694 A1 | 7/2011 | Leuthold | |
| 2014/0246611 A1 * | 9/2014 | Sacquard et al. | 250/559.1 |

FOREIGN PATENT DOCUMENTS

| | | |
|---|---|---|
| DE | 199 01 702 A1 | 7/2000 |
| DE | 102 34 431 A1 | 2/2004 |
| DE | 10 2004 039 049 A1 | 2/2006 |
| DE | 10 2006 052 798 A1 | 5/2008 |
| DE | 10 2007 037 923 A1 | 2/2009 |
| DE | 10 2008 009 375 A1 | 8/2009 |
| EP | 1 128 337 A1 | 8/2001 |
| GB | 2 109 923 A | 6/1983 |
| WO | 2004/104948 A1 | 12/2004 |

\* cited by examiner

SOILING CHECK OF THE WINDOW OF A MEASURING APPARATUS FOR CHECKING SHEET MATERIAL

BACKGROUND OF THE INVENTION

1. Field of the Invention

The present invention relates to a method for the soiling check of the window of a measuring apparatus for checking sheet material, a measuring apparatus which is formed for carrying out the method, and an apparatus for processing sheet material, which contains the measuring apparatus.

2. Description of Prior Art

Apparatuses for processing sheet material are apparatuses such as processing machines for value documents, for example bank note processing machines for checking bank notes, or other processing machines such as for example cash depositing machines and cash dispensing machines. There can be checked sheet material of any kind, in particular value documents, such as for example bank notes. In general, "sheet material" is to be understood to be sheet-shaped objects. With value documents there is the need to check them for authenticity, and value documents such as bank notes that are heavily used and become soiled thereby must be occasionally checked for their condition and if the soiling is too heavy withdrawn from circulation. For this reason, bank note processing machines check the bank notes for authenticity, but, partly, also for their condition, in particular for their soiling condition. Too heavily soiled bank notes are sorted out by the bank note processing machine and, where applicable, automatically destroyed in the machine, so that they are removed from circulation.

Since a preferred field of application of the present invention are bank note processing machines and the check of bank notes, the invention is described hereinafter with reference to bank note processing machines and measuring apparatus for checking bank notes. The present invention is by no means limited to this field of application, however, but can be used for the check of any sheet material.

In apparatuses for checking bank notes, the bank notes are usually irradiated on one or on both surfaces by means of at least one light source, and the remitted light and/or the transmitted light is detected by means of suitable optical sensors. For the protection of the sensors, between the transported bank notes and the sensors there are mostly windows that are transmissive for the employed wavelengths, in order to prevent a mechanical damage or a soiling of the sensors. In the course of time, however, these windows become soiled, so that the remitted light, which is detected by a sensor, not necessarily comes from the checked bank note, but possibly from a soiling of the measurement window. The result of the optical check of the bank notes may be distorted thereby. For example, the soiling, upon viewing along the transport direction of the bank note through the processing machine, leads to bright streaks on the detected bank note image. These streaks come about e.g. by scattered light of the locally soiled measurement window. The measurement window or the measurement windows are therefore cleaned, when a certain degree of soiling has been reached.

For ascertaining when a cleaning is necessary, the soiling of the measurement windows is regularly automatically checked during the operation of a bank note processing machine. For this purpose, the sensor detects, in the phases when no bank note is in its capture region, the remitted or the transmitted light. The established value is compared with a reference value for a clean window. When the difference exceeds a specified value, the need for cleaning is indicated or a cleaning is automatically carried out, for example through blown air directed onto the measurement windows. Alternatively, the measurement windows can be manually cleaned. Since the operation of the bank note processing machine usually must be interrupted for the cleaning, frequent manual or automatic cleaning work leads to a reduction of the bank-note throughput of the machine

SUMMARY OF THE INVENTION

It is therefore the object of the present invention to increase the throughput of bank note processing machines and other apparatuses for processing sheet material. It is in particular the object of the present invention to diminish the frequency of necessary cleaning work of the measurement windows. The quality of the measurements on the sheet material to be checked must not be declined through the diminished number of cleaning work.

The object is achieved by the method for the soiling check of the window of a measuring apparatus which is formed for checking sheet material. The check of the sheet material can be an optical check of the sheet material, e.g in order to ascertain the type of the sheet material and/or its condition and/or the authenticity of the sheet material. This sheet material are in particular value documents, for example bank notes. The object is further achieved by the measuring apparatus which is designed to carry out this method. The object is also achieved by the apparatus for processing sheet material, which contains the measuring apparatus. Developments of the invention are stated in the respective dependent claims.

The invention starts out from the idea that upon the check of sheet material, in many cases the sheet material is not checked over the full area, but only a partial region of the sheet material is checked, e.g. upon the check for authenticity, upon the check for the type, or for the condition of the sheet material. For example, upon a soiling check of value documents normally not both surfaces of the sheet material are checked over the full area for soiling. Rather, in each value document there are regions, in which a soiling is particularly disturbing, and other regions in which it can be tolerated, if necessary. On bank notes, the regions where a soiling is particularly disturbing can be, for example the unprinted bank note edge region, the white field of the bank note, portrait regions and the region with the bank note number. In order to diminish the effort upon the judgment of the degree of soiling, as a rule, for each value document there are defined one or several partial regions, in which a soiling check is to take place. The other regions of the value document are not checked for soiling. When on a surface of a value document several partial regions are checked for soiling, these partial regions can lie separated or overlap each other. Analogous to the soiling check, also for the authenticity check and/or the check of the type of the bank notes there can be defined one or several partial regions of a bank note that are to be checked.

An apparatus suitable for processing sheet material can be formed such that the sheet material is guided in rapid succession along a transport path through the apparatus and, in doing so, is also guided between two measurement windows of a measuring apparatus. On both sides of the measurement windows there are arranged one or several light sources and respectively an optical sensor of the measuring apparatus. These optical sensors have the form of sensor lines, they being for example image sensors, usually CMOS-, CCD- or photodiode lines. The sensor lines have at least the width of the sheet material to be checked. It is pointed out that for the purposes of the present invention the term "length" means the extent of an object in the transport direction of the sheet material, while the term "width" designates the extent of an object perpendicular to the transport direction of the sheet material. Accordingly, in case of the sensor lines one speaks of a "width", because they extend perpendicular to the transport direction.

From the light sources light of one or several certain wavelengths, which can lie in the visible region, in the UV- or IR-region, is irradiated through the measurement windows onto the surfaces of a sheet material being in the region relevant. The irradiated light is remitted by the surfaces, again passes the measurement windows and is finally received by the sensor line. From the sheet material transported past the measuring apparatus, in this way, there is recorded line by line an image. For checking the sheet material, from the detected signals of the sensor line there are evaluated only the signals of that light, however, that is remitted by the partial region of the sheet material that has been predefined in advance to be the partial region to be checked. The check limited to the partial region of the sheet material is e.g. a soiling check, an authenticity check, a check for the type of the sheet material or a different kind of check. Instead of in remission, the sheet material can also be measured in transmission, for example by means of a dark-field transmission measurement. Of course, it is also possible to provide light source and sensor lines only on one side of the sheet material transport path and to do without an opposite measuring apparatus.

In apparatuses for processing value documents, the value documents are usually transported through the apparatus to be directly succeeding one another, and after a certain number of transported value documents, the transport is respectively paused. During the transport pauses no value document is in the capture region of the sensor line, and the light received by the sensor line is the light that is remitted or transmitted either by the windows themselves or by soilings on the windows. This light is evaluated by an evaluation device and through a comparison with a reference value for clean measurement windows the soiling of the measurement window is established. If the established value exceeds a certain threshold value, a request for cleaning the windows is made or the operation of the apparatus is automatically stopped and a window cleaning is carried out.

The soiling of the windows can be measured in remission and/or in transmission, e.g. with the help of a dark-field transmission measurement. While with a remission measurement light source and sensor line are arranged on the same side of the window, with a transmission measurement they are arranged on opposite sides of the window. In transmission measurement, the light of the light source, for example visible light, UV- or IR-light, is irradiated through the measurement window, or with a symmetric arrangement through the measurement windows, and detected on the other side of the measurement window by the associated sensor line. By comparison with a reference value for clean measurement windows, the degree of soiling of the measurement window or measurement windows is determined.

The previous methods for determining the soiling of the measurement windows proceed such that the soiling of the windows is measured in value document transport pauses, and that, in addition, the measurement windows are checked for soiling over the entire window width. There thus also takes place a soiling check of the measurement windows in such regions which are easily allowed to be soiled, because upon the check of the value document, they are arranged above or below those partial regions of the value document that are not checked. When in one of these regions there is a soiling, there has been hitherto carried out a cleaning action.

In a top view of a bank note to be checked or another value document, to each partial region of the bank note, which is checked, there corresponds a substantially as wide partial region of the measurement window above or below the bank note, through which the irradiated or remitted or transmitted light passes upon the check of the bank note. In the present invention, in contrast to previous soiling checks of the measurement windows, the soiling check is now limited in targeted fashion to one or several partial regions of the measurement windows, namely to those partial regions of the measurement windows that actually play a role upon the check of the bank note to be respectively checked, i.e. through which the light remitted by the bank note or the light transmitted through the bank note passes, that is evaluated for the check of the bank note. A soiling of a measurement window outside the relevant partial region is not determined, i.e. it is not taken into account upon the soiling check, and therefore no cleaning action is prompted. Unnecessary cleaning actions due to a soiling in a region of a measurement window that is located outside the partial region that is relevant for the check of the bank note are avoided thereby, and this without any negative effects on the check of the bank notes. The invention therefore allows a reduction of cleaning actions, which leads to less interruptions of the operation and to an increased throughput of value documents such as bank notes.

In each measurement window, that partial region of the measurement window that is to be checked for soiling has, when viewed perpendicular to the transport direction of the bank note, a smaller width than the bank note width. The location and width of that partial region of a measurement window that is to be checked for soiling are chosen such that these approximately correspond to that partial region of the bank note that is to be checked, i.e. the light emanating from that partial region of the bank note that is to be checked falls through this partial region of the measurement window onto the sensor line. In accordance with a preferred embodiment, the width of the partial region of the measurement window, in which the measurement window is checked for soiling, is chosen to be somewhat greater than the width of the corresponding partial region of the bank note, e.g. in order to take into account transport fluctuations of the bank note. The narrower that partial region of the bank note that is used for the check thereof, the narrower that partial region of the windows can be chosen that is checked for soiling. The saving of cleaning actions achieved according to the invention are therefore the greater, the narrower the partial region or partial regions of the checked value documents are.

Upon the check of the soiling of the window, the location and width of the partial region of the window to be checked for soiling are chosen preferably in dependence on the type of the sheet material to be checked. In bank note processing machines, when for the different bank note types respectively one or several certain partial regions are provided for the check, the location and width of the measurement window partial region/s to be checked for soiling are chosen in dependence on the bank note type to be respectively checked. When the bank note processing machine is operated by denomination, i.e. when the bank notes to be checked all belong to the same type, according to the invention there is achieved a particularly great advantage, since in this case only that measurement window partial region is to be monitored for soiling, that corresponds to a certain bank note partial region. When the bank note processing machine is operated not by denomination, i.e. when bank notes of different types are checked for soiling, usually several measurement window partial regions must be checked for soiling, since the bank note partial regions checked in the different bank notes normally vary from bank note type to bank note type. The measurement window partial regions that must be included in the soiling check can overlap each other or be separate from each other, depending on the location and size of the corresponding bank note partial regions to be checked. Since the measurement window partial regions checked for soiling altogether are significantly narrower than the measurement windows, according to the invention there is achieved a saving of cleaning actions.

When the remitted light caused by the window soiling, which typically consists of light reflected by the soiling and scattered light, exceeds a certain intensity threshold, the operation of the machine can be automatically interrupted or, alternatively, a message can be output that a cleaning is necessary. It can also be provided that this threshold must be exceeded in several consecutive soiling checks, in order to prompt an interruption of operation of the machine or a message that a cleaning is necessary. With the interruption of operation of the machine there can also be triggered an automatic cleaning of the measurement window or of the measurement windows, for example by blown air.

These statements of course apply analogously, when for measuring the window soiling not the light remitted by the windows but the light transmitted through the windows is used. Here, too, according to the invention there are checked only those partial regions of the measurement windows for soiling, which play a role upon the check of the sheet material.

As already mentioned, the optical sensor employed for checking the sheet material is a sensor line, which extends over a width which corresponds to the width of the widest sheet material to be potentially checked. The check of the sheet material can be carried out as a remission measurement and/or as a transmission measurement. The soiling check of the measurement windows can also be carried out as a remission measurement and/or as a transmission measurement, the transmission measurement preferably being carried out as a dark-field transmission measurement. The spectral region employed for the check of the sheet material and for the check of the window soiling is preferably the same spectral region, i.e. light in the visible region, IR-region or UV-region. The measurements can be carried out "symmetrically", both surfaces of a sheet material being simultaneously checked for the respective properties. Also the measurement of the window soiling can be performed on both sides. The measuring apparatus for checking the sheet material can be formed substantially symmetrically with respect to light sources, sensors and, where applicable, filters and lens systems, with the sheet material transport path as the symmetry plane.

The soiling check of the measurement window takes place in phases, i.e. in such time segments, in which there is no sheet material in the capture region of the sensor line. With respect to the time flow of the check of the sheet material and the soiling check of the measurement windows, there are the possibilities as follows: The soiling check can be carried out as a separate measurement in a singling pause of the sheet material processing machine or during the sheet material check, in the gap between two sheets of the sheet material transported past the measuring apparatus. In doing so, there are two variants for the detection of the light remitted by the potentially soiled window or of the light transmitted through the window. Either, the light is detected over the entire width of the sensor line or of the sheet material, but from the detected light signals there are evaluated only those light signals which are due to that partial region of the window, that corresponds to the partial region of the sheet material that is relevant upon the check of the sheet material. In the second variant, from the start, only that light is detected, that is due to the window region that corresponds to the partial region which is relevant for the check of the sheet material.

Alternatively, the soiling check of the measurement window is not carried out as a separate measurement at a time, at which no sheet material is in the capture region of the sensor line. Rather, for the check of the sheets of a sheet material, each individual measurement of a sheet is carried out over a period somewhat longer than it would be necessary with the respective transport speed for recording an image of the sheet. The recorded image therefore contains not only the sheet itself, but covers, when viewed in transport direction, a region somewhat greater than the sheet, so that in the image there is also contained a section before or after the sheet. This section of the recorded image can therefore also be employed for the soiling check of the one or more measurement windows. For the soiling check of the measurement window in the partial region that is relevant for the check of the value document there is then evaluated a corresponding two-dimensional image region, which in the recorded image is arranged next to the value document, i.e. has been recorded temporally before or after the value document. The image region represents the window region that with respect to its width and location in the beam path of the light corresponds to the checked region of the sheet material, on the basis of which the sheet is checked for example for authenticity, type or usage state. The length of the image region along the transport direction can be arbitrarily selected, as long as the image region is completely present on the image and arranged outside the image of the sheet.

The advantage of this alternative is that singling pauses of the machine, that hitherto had to be made for the soiling measurement of the measurement windows, are omitted. Instead, the image recorded upon the check of a bank note (or any other sheet material) can be used to check the window soiling. A check of each bank note is usually not required, however. Rather, it is sufficient when in regular intervals, i.e. after a certain number of bank notes, a recorded image is picked out and evaluated for the window soiling check, for example every hundredth image. Alternatively, also a joint evaluation of several images of the relevant window partial regions can be carried out.

BRIEF DESCRIPTION OF THE DRAWINGS

The invention will hereinafter be explained further on the basis of Figures. It is to be understood, that the Figures only serve for illustrating the invention and are by no means to be understood as restrictive. The Figures are schematic and neither true to scale nor true to proportion. The same reference numbers designate the same or corresponding elements. In the Figures there are shown.

DETAILED DESCRIPTION OF PREFERRED EMBODIMENTS

Figure 1:
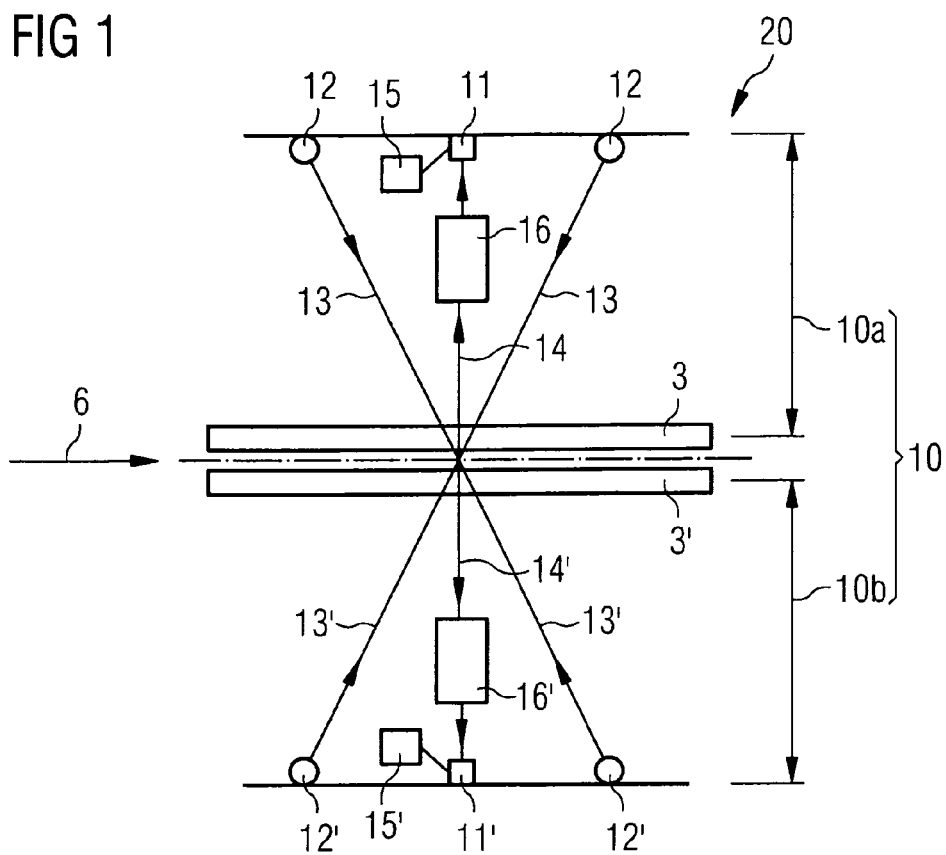
FIG. 1 a schematic representation of a sheet material processing apparatus according to the invention, having a measuring apparatus according to the invention for carrying out the soiling check according to the invention, in cross section, FIG. 2 a top view of a measurement window of a measuring apparatus according to the prior art, with value document arranged therebelow (FIG. 2b), and a top view of the sensor line thereof (FIG. 2a), and FIG. 3 a top view of a measurement window of a measuring apparatus according to the invention, with value document arranged therebelow (FIG. 3b), and a top view of the sensor line thereof (FIG. 3a), and FIG. 4 a top view of an image of a value document with that partial regions of the value document that are to be checked and with simultaneously recorded measurement window partial region according to an embodiment of the present invention.

FIG. 1 shows schematically and in cross section a measuring apparatus 10 which is contained in a sheet material processing apparatus 20. There are shown only those components of the processing apparatus 20 that are substantial for the present invention, namely the transport path 6 of the sheet material 1 to be checked and the measuring apparatus 10 for checking the sheet material that is transported on the transport path 6 through the processing apparatus 20. In the represented embodiment, the measuring apparatus 10 has two parts, i.e. it consists of a unit 10a and of a unit 10b, which are arranged on opposite sides of the transport path 6. This symmetrical arrangement is a preferred embodiment, because in this way the sheet material 1 can be checked from both sides simultaneously, but it is basically also possible to carry out the method according to the invention with a measuring apparatus 10 that consists only of the unit 10a or only of the unit 10b. Hereinafter, the check of the sheet material 1 and of the measurement window soiling is described on the basis of a remission measurement, but it is also possible that it is carried out on the basis of a transmission measurement.

The unit 10a of the measuring apparatus 10 according to the invention consists of two light sources 12, a lens system 16, a sensor line 11, an evaluation device 15 and a measurement window 3. The sheet material to be checked (not shown) is guided along the transport path 6, indicated by a dot-dashed line, through the apparatus 20. The arrow indicates the transport direction. Hereinafter, it is assumed that the sheet material are bank notes. In the course of the transport, the bank notes are guided past the measurement window 3 or between the measurement windows 3, 3', and, in doing so, are irradiated by the light sources 12 with the light 13, the light sources 12 being arranged such that they are oriented towards a predetermined position of the window 3. The light 13 impinges on the bank note transported past and is remitted to a certain part as light 14. The light 14 is detected by the sensor line 11 and converted to light signals, and a certain part of the light signals is evaluated by the evaluation unit 15 of the measuring apparatus 10. The sensor line 11 is for example a CMOS-, a CCD- or a photodiode line. The evaluation device 15 is for example a microprocessor. For the optical imaging it is preferred to provide a lens system 16 in front of the sensor line 11, for example linearly arranged gradient index lenses, which produce a 1:1 image on the sensor line 11.

The bank notes transported through the processing apparatus 20 are not checked over the full area, i.e. not on their entire surfaces. For example, upon a soiling check of the bank notes, only those partial regions of the surface are checked for soiling, in which such soilings are perceived to be particularly disturbing. For this reason, from the light signals that the sensor line 11 detects from the bank note transported past, not all are evaluated by the evaluation device 15, but an evaluation takes place only for certain light signals, namely for the light signals of the light that is remitted by that predetermined partial regions of the bank note that are to be checked for soiling. In addition to the soiling check in the viewed partial region of the bank note, the bank note can be simultaneously checked, on the basis of the light signals of the sensor line, also over its full area or in other partial regions for other properties, when the soiling of the measurement window impairs the check of these other properties less.

When there is no bank note in the beam path of the light 13, the light is nevertheless remitted to a certain part and detected by the sensor line 11. Responsible for this is the window 3 or that partial region of the window 3 that is located in the beam path of the light employed for checking the bank note. With a symmetric arrangement of the measuring apparatus 10 on both sides of the transport path 6 of the bank note, accordingly both windows 3, 3' are responsible. The stronger the soiling of these check-relevant partial regions of the windows, which lie in the light path of the light upon the check of the bank note, the more light is remitted and detected by the sensor line. The measurement window 3, as a rule, is somewhat wider than the widest value document that is to be checked with the measuring apparatus 10. The sensor line 11 extends transversely to the transport direction of the value documents and has at least the width of the widest value document that is to be checked.

Measuring apparatuses of the prior art are configured such that the sensor line 11, during the transport of the value document, continuously detects the light 14 impinging on it. In phases in which there is no bank note in the detection region of the sensor line 11, the light signals are hitherto evaluated over the entire width of the sensor line 11 by the evaluation device 15. When there is a soiling at any position in that region of the window 3 that lies in the beam path of the light, in the previous measuring apparatuses this position is taken into account and a cleaning of the window is carried out.

According to the invention, it has been found that with this procedure numerous unnecessary cleaning actions are carried out. The soiling often lies in a region of the window 3, which plays no role whatsoever upon the check of the bank note, because it does not lie in the beam path of the light between light source 12 and that partial region of the bank note that is to be checked or between that partial region of the bank note that is to be checked and the sensor line 11. A cleaning of the window 3 must only be carried out, when the check-relevant partial region of the window is soiled. In order to prompt the window cleaning, e.g. the evaluation device 15 ensures that the measuring apparatus 10 sends a corresponding signal to the apparatus 20.

The measuring apparatus 10 can be configured such that the sensor line 11 detects light signals over the entire region of its width, but the evaluation device 15 evaluates the light signals detected by the sensor line only for a specified partial region of the sensor line. Evaluated are, on the one hand, the light signals emanating from that partial region of the bank note that is to be checked, and, on the other hand, when there is no bank note in the detection region of the sensor line, the light signals emanating from that window region that lies, upon the check of the bank note, in the beam path of the evaluated light.

Alternatively, the measuring apparatus can be configured such that in phases, in which no bank note is present in the detection region of the sensor line, the sensor line 11 detects light signals only over a partial region of its width and the evaluation device evaluates these light signals detected by the sensor line. Also in this way, it is achieved that, when no bank note is in the detection region of the sensor line, only those light signals are evaluated that are emanated from that window region which, upon the check of the bank note, lies in the beam path of the light that is evaluated for the check. In any case, soilings in window regions that play no role upon the check of the bank note are not taken into account, and unnecessary cleaning actions of the windows are therefore avoided.

The mode of functioning of the measuring apparatus 10 has been described above on the basis of unit 10a. The unit 10b having the light sources 12', the sensor line 11', the evaluation device 15', the lens system 16' and the measurement window 3' works analogously. The light sources 12' are arranged such that they direct light 13' onto the same position of the bank note, onto which the light 13 of the light sources 12 is directed, but from the opposite direction, so that the other surface of the transported sheet material 1 can be checked. The sheet material 1 remits light 14', which is detected by the sensor line 11' and evaluated by the evaluation device 15'. In the absence of sheet material 1, the light 14' is remitted by the windows, so that these can be checked for soiling.

The measuring apparatus 10 is also suitable for the soiling check in transmission. Upon a measurement in transmission, the light sources 12 irradiate measuring light 13 onto the window 3 and the bank note guided past, and the transmitted light is detected as light 14' by the sensor line 11' and evaluated by an evaluation device 15'. If there is no bank note in the detection region of the sensor line 11', in the transmission measurement there is measured, in a way completely analogous to the remission measurement, the soiling of the measurement window 3, 3'. The transmission measurement is preferably carried out as a dark-field transmission measurement, i.e. the sensor line 11' is not in the direct beam path of the light emitted by the light sources 12, but in an angle thereto, e.g. FIG. 1.

Figure 2A:
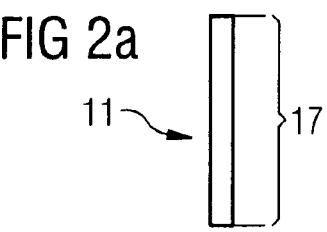
Figure 2B:
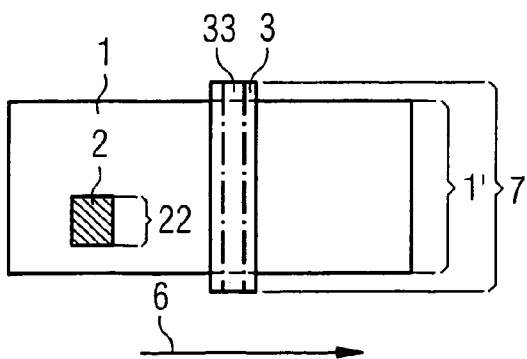

FIG. 2b shows a top view of the measurement windows 3 of a measuring apparatus 10a in a phase in which a bank note 1 is below the measurement window 3. Here, only the partial region 2 of the bank note 1 is checked. The bank note 1 has a width 1' and the measurement window 3 has a width 7, which is somewhat greater than the width 1' of the bank note. With dot-dashed lines there is represented that region 33 of the window, through which the light 14 passes that emanates from the bank note 1 and is detected by the sensor line 11 for checking the bank note. The sensor line 11 represented in FIG. 2a, in the top view of FIG. 2b would be arranged in front of the window 3. It has a width 17, which is somewhat greater than the width 1' of the bank note, and as a rule is about as great as the width 7 of the window.

While the bank note 1 is transported past the window, the sensor line 11 detects the light remitted by the bank note, i.e. it records line by line an image of the bank note. For checking the bank note, however, the detected light signals are only evaluated for that time interval in which the light 14 emanating from the partial region 2 to be checked reaches the sensor line 11. Since the partial region 2 has a relatively small width 22, only a proportion of the total light impinging on the sensor line 11 is evaluated for checking the bank note.

Subsequently, the next bank note is guided past the measurement window. Between two bank notes or other sheet material there is respectively a short detection pause of the sensor line 11. These detection pauses can be used to check whether the measurement windows are possibly dirty. According to the prior art, for this purpose, light is irradiated on the measurement window 3 in the same way as upon the check of the sheet material, and the remitted or the transmitted light is detected by the sensor line 11 and evaluated by the evaluation device 15. For the soiling check of the measurement window 3 there is hitherto evaluated the entire light that the sensor line 11 detects, i.e. the entire light remitted by the region 33 or transmitted through the region 33. Soilings of the region 33 are only disturbing, however, when they are located in that part of the region 33 that with respect to its location in the beam path of the light corresponds to the region 2 of the sheet material 1. This region has only a width 22, and with all the soilings that are located outside the region concerned, according to the prior art a window cleaning is carried out nevertheless.

Figure 3A:
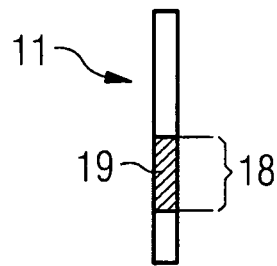
Figure 3B:
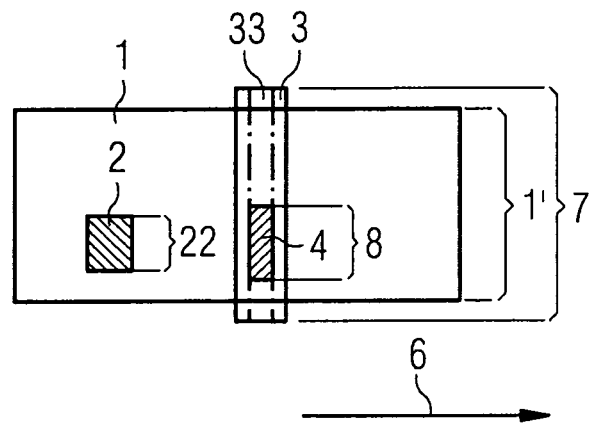

The solution according to the invention is illustrated in FIG. 3b. In FIG. 3b, again, a top view of a measurement window 3 having a width 7 is represented in a phase in which a bank note 1 is transported in transport direction 6 past the measurement window 3 and, in so doing, is examined. The bank note 1 has the width 1' and a partial region 2 to be checked with a width 22. That region of the window 3 through which the light to be detected by the sensor line 11 passes, is again designated with the reference number 33 and represented in dot-dashed fashion. In FIG. 3a, there is represented the sensor line 11, which in the top view of FIG. 3b would be located in front of the window region 33.

According to the invention, now the check of the bank note 1 is carried out in principle as explained in connection with FIG. 2, and also according to the invention, the phase or the time segment between two value documents is used to check the window soiling. Deviating from the previous procedure, however, there is evaluated not the entire light that reaches the sensor line 11 through the window region 33, but there is evaluated only a part of this light, namely the light that passes through that partial region 4 of the window, through which, upon the check of the bank note 1, the light employed for checking the bank note reaches the sensor line 11. With respect to its width and with respect to its location in the beam path of the light, the partial region 4 of the window corresponds to the checked partial region 2 of the bank note 1. This partial region 4 of the window has a width 8, which can be equal to the width 22 of the partial region 2 of the bank note, but can also be chosen to be somewhat greater, for example up to about 10% greater, in order to compensate transport fluctuations upon the transport of the bank notes. In this way, all the soilings of the window 3, which lie outside the partial region 4 of the window, are not taken into account. Thus, it is possible to save a plurality of unnecessary cleaning actions.

Alternatively, it is also possible that in the phases in which the soiling check of the window is carried out only a partial region of the sensor line 11 is activated, i.e. the partial region 19 having the width 18. The partial region 19 is that partial region of the sensor line 11 that detects the light that emanates from the partial region 2 upon the check of the bank note and that accordingly emanates from the partial region 4 upon the soiling check of the windows. The region 19 has a width 18, which is at least as great as the width 22 of the partial region 2, but preferably the partial region 19 is somewhat wider, in order to compensate possible transport fluctuations of the bank note 1. The width 18 is advantageously chosen to be about as great as the width 8 of the window partial region 4, i.e. up to about 10% greater than the width 22.

Alternatively, also for the check of the sheet material 1 it is possible that only the partial region 19 of the sensor line 11 is activated for the detection of light signals, and only the light signals detected by the region 19 are evaluated for the check of the sheet material 1 by the evaluation device 15.

The sheet material to be checked is usually scanned over the full area by the sensor line 11 of the measuring apparatus 10, in order to check also other properties of the sheet material. For example, the authenticity and/or the type of the sheet material is checked over the full area, but the soiling of the sheet material only in the partial region 2. Usually, each measurement is carried out somewhat longer than it would correspond to the length of the sheet material to be checked. I.e. the scanning begins already at a point in time at which there is not yet any sheet material, for example a bank note, in the detection region of the sensor line 11, and it ends only at a point in time that lies after the point in time at which the sheet material has left the detection region of the sensor line 11. The images recorded by a sensor line 11 are therefore longer than the image of the sheet itself, and the sheet image is flanked, when viewed in transport direction, on both sides by a hitherto "unused edge region". The image region next to the sheet image can now be advantageously employed for the soiling check of the measurement windows.

Figure 4:
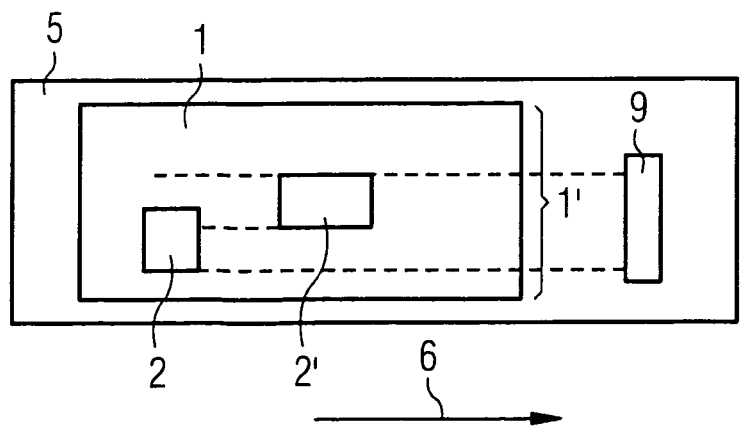

The image 5 recorded upon the scanning is represented in FIG. 4. The bank note 1 is here again transported in the direction of the arrow 6 through the sheet material processing apparatus 20 and, in doing so, the image 5 is recorded for the check of the bank note 1. Since the detection of the light 14 already begins before the bank note 1 reaches the detection region of the sensor line 11, the sensor line 11 automatically detects, until the arrival of the bank note 1 in the detection region of the sensor line 11, the e.g. scattered light emanating from the measurement window 3. According to a preferred embodiment, an image region before the actual measurement of the bank note (in FIG. 4 represented on the right-hand side) and/or an image region after the actual measurement of the bank note (in FIG. 4 this would be on the left of the bank note) is used for the soiling check of the windows 3. In doing so, the procedure is basically as explained above, i.e. the measurement can be made both in remission and in transmission, and only that partial region of the measurement windows 3 is checked for soiling, that with respect to its width and its location in the beam path of the light corresponds to the checked partial region of the bank note. This partial region is either predefined by the light impinging on the sensor line 11 being detected over the entire width 17 of the sensor line, but being evaluated only for a region 19 (as represented in FIG. 3a), or by the light impinging on the sensor line 11 being detected, from the start, only in the region 19, and therefore its evaluation to be made by the evaluation device 15 being possible only for the region 19.

In FIG. 4, there is represented a bank note 1, in which a partial region 2 and a partial region 2' are to be checked for soiling. The two partial regions overlap each other, but in total they are wider than each of the partial regions taken alone. In such a case, a window region must be checked for soiling, which with respect to its width and its location in the beam path of the light corresponds to the location and the total width of the partial regions 2, 2', or is somewhat greater, in order to compensate, where applicable, transport fluctuations of the bank note 1. In FIG. 4 the checked window region is represented as image region 9, it being apparent that the image region 9 has a width that is somewhat greater than the total width of the partial regions 2 and 2', but is still considerably narrower than the width of the value document 1, so that here, too, a saving of cleaning processes is achieved. A cleaning of the windows 3 is only prompted, when in the recorded image region 9 of the windows 3 a soiling is ascertained. Through this integration of the soiling measurement of the window into the time period for the recording of the image of the bank note, it is achieved, that no breaks for a soiling measurement of the window are required, which advantageously increases the bank note throughput of the processing machine.

The invention claimed is:

1. A method for a soiling check of a window of a measuring apparatus that is formed for checking a sheet material that is transported along a transport path past the measuring apparatus, and which has
at least one light source for irradiating the sheet material,
at least one sensor line for detecting a light emanating from the sheet material, the sensor line having at least the width of the sheet material,
at least one evaluation device for the evaluation of a light signal that was detected by the sensor line upon the detection of the light, and
at least one window between the sensor line and the transport path of the sheet material,
wherein in phases in which the sheet material is in a detection region of the sensor line, the method comprises the measuring apparatus carrying out a check of the sheet material, upon which there is checked only at least one partial region of each sheet of the sheet material, which partial region has a specified length and width and altogether is narrower than the width of the sheet material, through detection and evaluation of a light emanating from the at least one partial region of the sheet, and
wherein in phases in which no sheet material is in the detection region of the sensor line, a light emanating from the window is detected and evaluated for the soiling check of the window,
wherein, the soiling check of the window does not evaluate the entire area of the window but only evaluates a light that emanates from a partial region of the window through which, upon the check of the sheet material, the light reaches the sensor line and which with respect to its width and its location in a beam path of the light corresponds to that at least one partial region of the sheet material that is checked upon the check of the sheet material.

2. The method according to claim 1, wherein, for the check of the sheet material there is respectively recorded an image of a sheet of the sheet material, which image has a greater length than the sheet, and for the soiling check of the window there is evaluated an image region arranged next to the sheet on the image, which image region represents that partial region of the window, through which, upon the check of the sheet material, the light reaches the sensor line and which with respect to its width and its location in the beam path of the light corresponds to the at least one checked partial region of the sheet material.

3. The method according to claim 1, wherein the light emanating from the partial region of the window is a light remitted by the window and/or a light transmitted through the window.

4. The method according to claim 1, wherein the partial region of the window, from which partial region the light emanates that is evaluated for checking a soiling of the window, has a smaller width than the width of the checked sheet material.

5. The method according to claim 1, wherein the partial region of the window, from which partial region the light emanates that is evaluated for checking a soiling of the window, has a smaller width than the region of the window through which, upon the check of the sheet material, light reaches the sensor line.

6. The method according to claim 1, wherein, upon the check of the soiling of the window, the location and width of that partial region of the window that is to be checked for soiling is chosen in dependence on the type of the checked sheet material.

7. The method according to claim 1, wherein at least two partial regions of each sheet of the sheet material are checked by the measuring apparatus, and that a partial region of the window is checked for soiling, through which partial region, upon the check of the sheet material, the light reaches the sensor line and which with respect to its width and its location in the beam path of the light corresponds to the checked partial regions of the sheet material, which partial regions, however, have a smaller width than that region of the window through which, upon the check of the sheet material, light reaches the sensor line.

8. The method according to claim 1, wherein, upon the check of the sheet material, from each sheet of the sheet material there is recorded an image, which has a greater length than the sheet material, and for the check of a soiling of the window of the measuring apparatus, either the image of each sheet of the sheet material is evaluated or at regular intervals an image of a sheet of the sheet material is evaluated or the images of several sheets of the sheet material are evaluated together.

9. The method according to claim 1, wherein by the measuring apparatus there is automatically prompted, in dependence on a result of the soiling check, a cleaning of the window, in particular when the soiling of the window, ascertained upon the soiling check, exceeds or exceeds several times in succession a predefined threshold value.

10. A measuring apparatus for checking sheet material that for its check is transported along a transport path past the measuring apparatus, comprising
at least one light source for irradiating the sheet material,
at least one sensor line for detecting a light emanating from the sheet material, which sensor line has at least the width of the sheet material,
at least one window that is arranged between the sensor line and the transport path of the sheet material,
at least one evaluation device for evaluating light signals that are detected by the sensor line upon the detection of the light,
wherein the window, the light source and the sensor line are arranged such that upon operation of the measuring apparatus the light source radiates light on the window and, where applicable, the sheet material arranged adjacent the window, and the sensor line detects a light emanating from the window and, where applicable, the sheet material, and the evaluation device for checking the sheet material is designed to check only at least a partial region of the sheet material to be checked, which partial region has a specified length and width, but altogether is narrower than the width of the sheet material, through detection and evaluation of a light emanating from the at least one partial region of the sheet material,
wherein the evaluation device is configured, for the soiling check of the window, to not evaluate the entire area of the window but only to evaluate a light that emanates from a partial region of the window, through which, upon the check of the sheet material, the light reaches the sensor line, and which with respect to its width and its location in a beam path of the light corresponds to the at least one checked partial region of the sheet material.

11. The measuring apparatus according to claim 10, wherein the measuring apparatus is configured to record, for the check of the sheet material, an image of a sheet of the sheet material, which image has a greater length than the sheet, and that the evaluation device is configured to evaluate, for the soiling check of the window, an image region arranged next to the sheet on the image, which image region represents that partial region of the window, through which, upon the check of the sheet material, the light reaches the sensor line and which furthermore with respect to its width and its location in the beam path of the light corresponds to that at least one partial region of the sheet material that is to be checked.

12. The measuring apparatus according to claim 10, wherein the measuring apparatus is formed for measuring the remission of the sheet material and the light remitted by the window, and/or that the measuring apparatus is formed for measuring the transmission of the sheet material and the light transmitted through the window.

13. The measuring apparatus according to claim 12, wherein it is designed, for the check of a soiling of the window, to evaluate an image of each sheet of the sheet material or to evaluate at regular intervals an image of a sheet of the sheet material or to evaluate the images of several sheets of the sheet material together.

14. The measuring apparatus according to claim 10, wherein it is configured to automatically prompt, in dependence on a result of the soiling check, a cleaning of the window, in particular when the evaluation device ascertains, upon the soiling check, a soiling of the window that exceeds or exceeds several times in succession a predefined threshold value.

15. An apparatus for processing sheet material, in particular value documents, which is designed to transport sheet material along a transport path, wherein the apparatus has a measuring apparatus according to claim 10, wherein the measuring apparatus is arranged on one side or on both sides of the transport path.

* * * * *